(12) United States Patent
Karmhag et al.

(10) Patent No.: US 7,808,692 B2
(45) Date of Patent: Oct. 5, 2010

(54) MANUFACTURING OF CURVED ELECTROCHROMIC DEVICES

(75) Inventors: Richard Karmhag, Uppsala (SE); Greger Gustavsson, Uppsala (SE)

(73) Assignee: Chromogenics Sweden AB, Uppsala (SE)

( * ) Notice: Subject to any disclaimer, the term of this patent is extended or adjusted under 35 U.S.C. 154(b) by 80 days.

(21) Appl. No.: 12/375,479

(22) PCT Filed: Jul. 25, 2007

(86) PCT No.: PCT/SE2007/050535
§ 371 (c)(1), (2), (4) Date: Jan. 28, 2009

(87) PCT Pub. No.: WO2008/013500
PCT Pub. Date: Jan. 31, 2008

(65) Prior Publication Data
US 2009/0262411 A1 Oct. 22, 2009

(30) Foreign Application Priority Data
Jul. 28, 2006 (SE) .................................. 0601623

(51) Int. Cl.
*G02F 1/15* (2006.01)
(52) U.S. Cl. ..................... 359/265; 359/267
(58) Field of Classification Search ................ 359/265
See application file for complete search history.

(56) References Cited

U.S. PATENT DOCUMENTS

| | | | |
|---|---|---|---|
| 5,724,187 A | 3/1998 | Varaprasad et al. | |
| 5,805,367 A | 9/1998 | Kanazawa | |
| 5,953,150 A | 9/1999 | Smarto et al. | |
| 5,959,762 A | 9/1999 | Bandettini et al. | |
| 6,074,066 A * | 6/2000 | Macher et al. | 359/601 |

(Continued)

FOREIGN PATENT DOCUMENTS

EP 0950568 A1 10/1999

(Continued)

OTHER PUBLICATIONS

International Search Report dated Nov. 27, 2007, form corresponding PCT application.

(Continued)

*Primary Examiner*—Jordan M. Schwartz
*Assistant Examiner*—James C Jones
(74) *Attorney, Agent, or Firm*—Young & Thompson (57) ABSTRACT

A method of manufacturing permanently curved electrochromic devices is presented. The method includes provision (210, 211) of two plane thermoplastic substrates at least partly coated by an electron conducting layer. The substrates are further at least partially coated (220, 221) with an electrochromic or a counter electrode layer. The coated substrates laminated (230) together with an adhesive electrolyte layer in the middle into an electrochromic laminate sheet. The electrochromic device is formed (240) by thermoforming the covered substrates into a permanent curvature, prior or after the further coating, prior to the laminating of the substrates or by thermoforming the electrochromic laminate sheet after the lamination. Once formed, the coated substrates or electrochromic device, respectively, permanently remains in its curved shape. Additional layer, such as bus bars and layers for chemically adaptation can be provided onto the substrates prior or after the thermoforming step.

11 Claims, 11 Drawing Sheets

U.S. PATENT DOCUMENTS

| | | | |
|---|---|---|---|
| 6,211,995 | B1 | 4/2001 | Azens et al. |
| 6,404,532 | B1 | 6/2002 | Berneth et al. |
| 6,500,287 | B1 | 12/2002 | Azens et al. |
| 7,012,729 | B2 * | 3/2006 | Tonazzi et al. ............... 359/265 |
| 2003/0052838 | A1 | 3/2003 | Kim et al. |
| 2004/0253401 | A1 | 12/2004 | Pratt et al. |

FOREIGN PATENT DOCUMENTS

| | | |
|---|---|---|
| WO | 99/23528 | 5/1999 |
| WO | 99/32917 | 7/1999 |

OTHER PUBLICATIONS

Azens A et al: "Flexible foils with electrochromic coatings: science, technology and applications" Materials Science and Engineering B, Elsevier Sequoia, Lausanne, CH, vol. 119, No. 3, Jun. 15, 2005, pp. 214-223.

Granqvist C G: "Electrochromic devices" Journal of the European Ceramic Society, Elsevier Science Publishers, Barking, Essex, GB, vol. 25, No. 12, Apr. 5, 2005, pp. 2907-2912.

Extended European Search Report in Corresponding Application EP 07 79 4145 dated Dec. 9, 2009.

Granqvist, C. G., "Handbook of Inorganic Elechtrochromic Materials", 2002, pp. 19-63, Chapters 2-4, Elsevier.

* cited by examiner

Fig. 7B

MANUFACTURING OF CURVED ELECTROCHROMIC DEVICES

TECHNICAL FIELD

The present invention relates in general to manufacturing of electrochromic devices and in particular to manufacturing of curved electrochromic devices.

BACKGROUND

The surface curvature is of critical importance to the performance of most optical devices. For instance, the focal plane of a curved mirror is determined by the mirror curvature and a refractive lens derives its ability to converge or diverge light from the difference in the curvature of the front and the rear surface. Singly curved optical devices have a surface presenting a curvature in one direction along the surface. Doubly curved optical devices have a surface presenting a curvature in all directions along the surface. Non-exclusive examples of curved optical devices are visors, goggles, rear view mirrors, automotive windows, skylights and headlamps.

In many of these examples, electrochromic devices are of interest for achieving a controllable color and/or transmission. A typical electrochromic device comprises five superimposed layers deposited on one substrate or positioned between two substrates in a joined together configuration. The central part of the five-layer electrochromic stack is an ion conductor (electrolyte). The ion conductor is in contact with an electrochromic film, capable of conducting electrons as well as ions. On the other side of the ion conductor is an electron and ion conducting counter electrode film serving as an ion storage layer. The central three-layer structure is positioned between electron conducting layers. Such a device is colored/bleached by applying an external voltage pulse between the electron conducting layers on the two sides of the stack, causing the electrons and ions to move between the electrochromic layer and the counter electrode layer.

Applications of electrochromic devices include architectural windows, information displays, light filters and modulators, rear-view mirrors, sunroofs and windows in vehicles, eyewear, helmet visors, ski goggles, surfaces with variable thermal emissivity or camouflage. Many of these applications present doubly curved surfaces.

Historically, the first electrochromic coatings were deposited on glass substrates. The possibility of using plastic substrates is described, for example, in WO9923528. Electrochromic devices on plastic substrates are characterized by their light weight, flexibility, and the ease of cutting to complex shapes.

The principal prior art sequence of producing curved electrochromic devices comprises the following steps. It starts with provision of two complementary substrates. The substrates are preformed into a permanent curved shape. Both substrates are coated with electron conducting layers, one substrate is coated with an electrochromic layer and the other substrate is coated with a counter electrode layer. Additional layers, such as bus bars, may also be included in the stack. The two matching substrates are laminated with an electrolyte between them to form an electrochromic device. Finally the edges are sealed.

There are many prior art disclosures presenting different types of doubly curved electrochromic devices. Just a few examples will be presented here. The U.S. Pat. No. 5,953,150 discloses a method for producing doubly curved electrochromic devices for eyeglass lenses. Two half cells, one concave and one convex, are put together with an ion-conducting polymer between.

The published US patent application 2004/0253401 discloses a method of making a curved electrochromic device for portable electronic devices. A compound curved shaped housing part includes integrated activatable electrochromic indicia. The indicia are formed by coating an internal surface of a transparent plastic shell with a sequence of layers including: optionally a separate transparent conductor, an electrochromic material layer, an electrolyte layer, optionally a separate ion donor layer, optionally an insulator layer and a second conductive layer. The electrochromic material is deposited onto pre-curved substrates.

In the U.S. Pat. No. 5,805,367 a transparent electrode formed by an ITO film, an EC layer of an optoelectronic comprising element, a reflecting film also serving as an electrode thin film and an insulating sealing film are deposited on a rear surface of a transparent substrate of a main member of a mirror. The transparent substrate has dividing lines for dividing a mirror surface area into a main mirror surface area of a certain curvature convex surface having a large radius curvature and a supplemental mirror surface area of a gradually varied curvature convex surface having a gradually decreased radius curvature.

SUMMARY

A general problem with prior art manufacturing of double curved electrochromic devices is that it is generally very difficult to produce coatings with uniform thickness on a doubly curved substrate. Moreover, upon sputtering, areas closer to the target are more exposed to heat, which may be devastating for most thermoplastic substrates. Furthermore, large production volumes are difficult to achieve for coating of curved surfaces and objects with curved shapes are generally difficult to handle, store and ship.

A general object of the present invention is therefore to provide an improved method for manufacturing of electrochromic devices. A further object of the present invention is to allow for efficient coating of electrochromic device substrates intended for curved electrochromic devices.

The objects presented here above are achieved by manufacturing methods and devices according to the present claims. In general words, a method of manufacturing permanently curved electrochromic devices is presented, which comprises a step of providing two plane thermoplastic substrates at least partly coated by an electron conducting layer. The substrates are further at least partially coated with an electrochromic or a counter electrode layer. The coated substrates laminated together with an adhesive electrolyte layer in the middle into an electrochromic laminate sheet. The electrochromic device is formed by thermoforming the coated substrates into a permanent curvature, prior or after any further coating, prior to the laminating of the substrates or by thermoforming the electrochromic laminate sheet after the lamination. Once formed, the coated substrates or electrochromic device, respectively, permanently remains in its curved shape. Additional layers, such as bus bars and layers for chemical adaptation can be provided onto the substrates prior or after the thermoforming step. Sealing and cutting steps are preferably performed in connection with the above described steps, and the thermoforming can be performed before or after any such step. Also outer layers intended to modify the surface of an electrochromic device can be provided onto the electrochromic device prior or after the thermoforming step.

One advantage with the present invention is that it at least partially removes problems with coatings with non-uniform thickness on a curved substrate, by ensuring that difficult coating procedures are performed on a flat substrate and then form the substrate into its final curved shape. For instance, in such a way the present innovation allows sputtering as a deposition technique for manufacturing curved electrochromic devices with thermoplastic substrates. From a mass-manufacturing point of view, coating and lamination of flat thermoplastic substrates can according to the present invention be performed in a roll to roll process for subsequent thermoforming into curved shapes and are thus well compatible with large production volumes. Also, flat substrates and devices are easier to handle, store and ship in comparison with curved substrates and devices.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the present disclosures, equal or directly corresponding features in different figures and embodiments will be denoted by the same reference numbers.

Electrochromic materials are in the present disclosure defined as materials that are able to change their optical properties, persistently and reversibly, under insertion/extraction of ions and electrons. An electrochromic layer is subsequently a layer comprising an electrochromic material.

Figure 1:
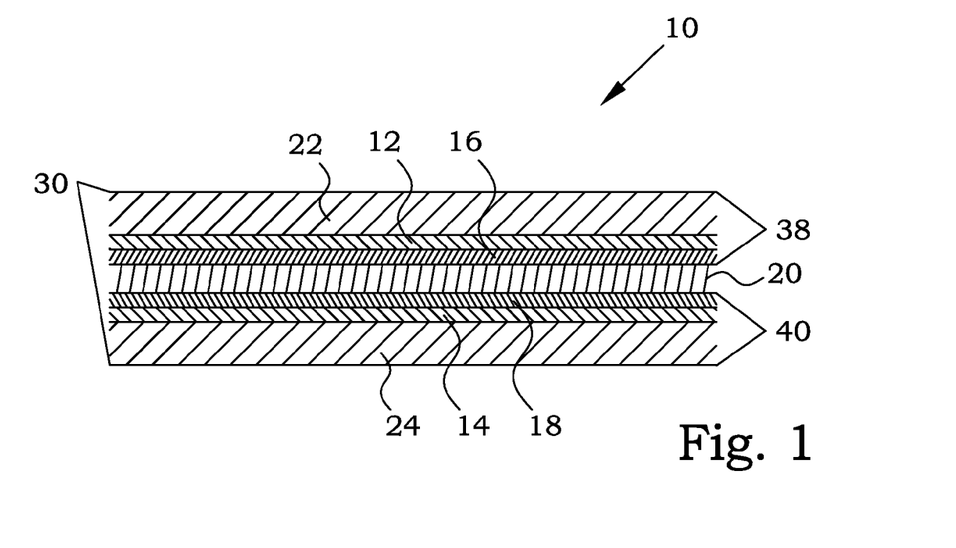
FIG. 1 is schematic illustration of a typical composition of an electrochromic device.

FIG. 1 illustrates a typical configuration of an electrochromic device 10. In the centre part, an ion conductor, i.e. an electrolyte layer 20 is provided. The electrolyte layer 20 is on one side in contact with an electrochromic layer 16, capable of conducting electrons as well as ions. On the other side of the ion conductor 20 is an electron and ion conducting counter electrode layer 18, serving as an ion storage layer. This counter electrode film 18 may entirely or partly be constituted by a second electrochromic film. The central three-layer structure 16, 18, 20 is positioned between electron conducting layers 12, 14. The electron conducting layers 12, 14 are arranged against outer substrates, in the present invention a first 22 and a second 24 plastic substrate. The stack of the plastic substrates 22, 24 and the central five layers 12, 14, 16, 18, 20 forms an electrochromic laminate sheet 30.

An "electrochromic half cell" 38, 40 consists of at least a substrate material coated with an electron conducting layer and an electrochromic layer or a counter electrode.

Such an electrochromic device 10 is colored/bleached by applying an external voltage pulse between the electron conducting layers 12, 14 on the two sides of the stack 30, causing the electrons and ions to move between the electrochromic layer 16 and the counter electrode layer 18. The electrochromic layer 16 will thereby change its color. Non-exclusive examples of electrochromic layers 16 are cathodically coloring thin films of oxides based on tungsten, molybdenum, niobium, titanium, lead and/or bismuth, or anodically coloring thin films of oxides, hydroxides and/or oxy-hydrides based on nickel, iridium, iron, chromium, cobalt and/or rhodium.

The optical modulation in the electrochromic films is achieved by insertion and extraction of ions. Hence, a porous microstructure is of greatest importance. The structure is discussed in detail by professor C. G. Granqvist in "Handbook of inorganic electrochromic materials", pp. 19-63 (chapter 2-4), Elsevier 2002.

At least one of the plastic substrates 22, 24 has to be transparent, in order to reveal the electrochromic properties of the electrochromic layer 16 to the surroundings. In the most general sense, a plastic substrate 22, 24 is a synthetic or semisynthetic polymerization product. The plastic substrate is commonly classified by its polymer backbone. Non-exclusive examples of possible plastic substrates are polycarbonates, polyacrylics, polyurethanes, urethane carbonate copolymers, polysulfones, polyimides, polyacrylates, polyethers, polyester, polyethylenes, polyalkenes, polyimides, polysulfides, polyvinylacetates and cellulose-based polymers Also at least one of the two electron conducting layers 12, 14 must be transparent. Non-exclusive examples of electron conductors 12, 14 transparent to visible light are thin films of Indium Tin oxide (ITO), Tin oxide, Zinc oxide, Titanium oxide, n- or p-doped Zinc oxide and Zinc oxyfluoride. Metal-based layers, such as ZnS/Ag/ZnS and carbon nanotube layers have been recently explored as well. Depending on the particular application, one or both electron conductor layers 12, 14 may be made of or include a metal grid.

The counter electrode layer 18 may, as mentioned above, comprise electrochromic materials as well as non-electrochromic materials. Non-exclusive examples of counter electrode layers 18 are cathodically coloring electrochromic thin films of oxides based on tungsten, molybdenum, niobium, titanium, lead and/or bismuth, anodically coloring electrochromic thin films of oxides, hydroxides and/or oxy-hydrides based on nickel, iridium, iron, chromium, cobalt and/or rhodium, or non-electrochromic thin films e.g. of oxides based on vanadium and/or cerium as well as activated carbon. Also combinations of such materials can be used as a counter electrode layer 18.

The electrolyte layer 20 comprises an ion conductor material. The electrolyte layer 20 may be transparent or non-transparent, colored or non-colored, depending on the application. Some non-exclusive examples of electrolyte types are: solid polymer electrolytes (SPE), such as poly(ethylene oxide) with a dissolved lithium salt; gel polymer electrolytes (GPE), such as mixtures of poly(methyl methacrylate) and propylene carbonate with a lithium salt; composite gel polymer electrolytes (CGPE) that are similar to GPE's but with an addition of a second polymer such a poly(ethylene oxide), and liquid electrolytes (LE) such as a solvent mixture of ethylene carbonate/diethyl carbonate with a lithium salt; and composite organic-inorganic electrolytes (CE), comprising an LE with an addition of TiO2, silica or other oxides. Some non-exclusive examples of lithium salts used are LiTFSI [lithium bis(trifluoromethane) sulfonimide], LiBF4 [lithium tetrafluoroborate], LiAsF6 [lithium hexafluoro arsenate], LiCF3SO3 [lithium trifluoromethane sulfonate], and LiClO4 [lithium perchlorate].

Additional layers, such as bus bars and layers for chemically adaptation can be provided onto the substrates. Also outer layers intended to modify the surface of an electrochromic device can be provided onto the electrochromic device.

Note that the relative thicknesses of the layers in the different figures in the present disclosure do not represent the true relationship in dimensions. Typically, the substrates are much thicker than the other layers. The figures are drawn only for the purpose to illustrate connection principles, not to give any dimensional information.

Electrochromic devices manufactured according to the present invention present curved surfaces. As mentioned further above, the surfaces can be single or double curved. An explanation of the terms "single curved" and "double curved" can be made with reference to FIGS. 2A-C.

A general surface has a tangential plane defined in each point. A flat surface coincides with the tangential plane in each point.

Figure 2A:
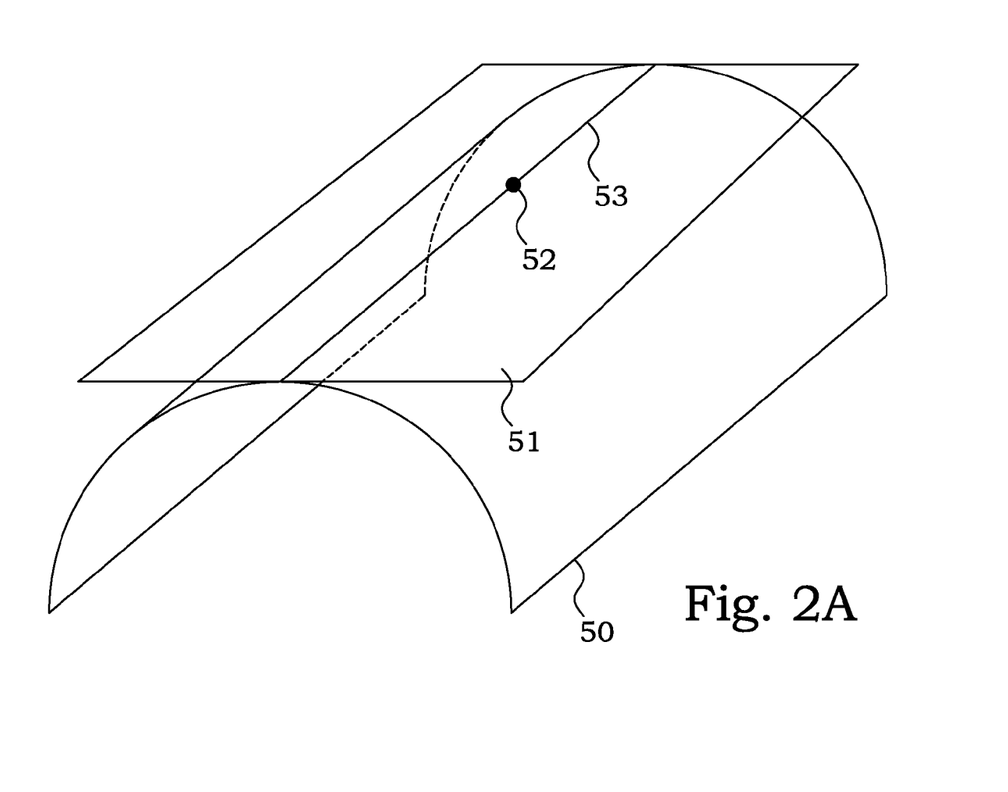
FIG. 2 is an illustration of singly and doubly curved surfaces.

A single curved surface has permanently a non-flat shape with at least one principal curvature. If a surface 50 is "single" curved, a tangential plane 51 defined at any point 52 is in contact with the surface 50 along at least one straight line 53, as shown in FIG. 2A. Examples of such "single curved" geometrical shapes are e.g. cylinders or cones. They are typically possible to form with any plastic reshaping. In many cases single curved surfaces are also possible to form by elastic deformation and attachment to a frame structure. However, the present invention relates to thermoforming of electrochromic devices, i.e. electrochromic devices having a permanent curved shape.

Figure 2B:
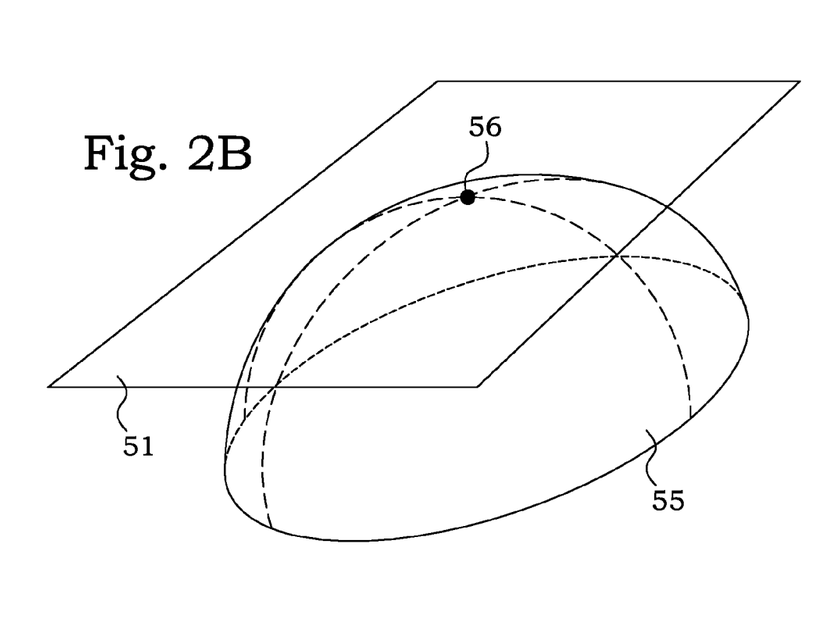
Figure 2C:
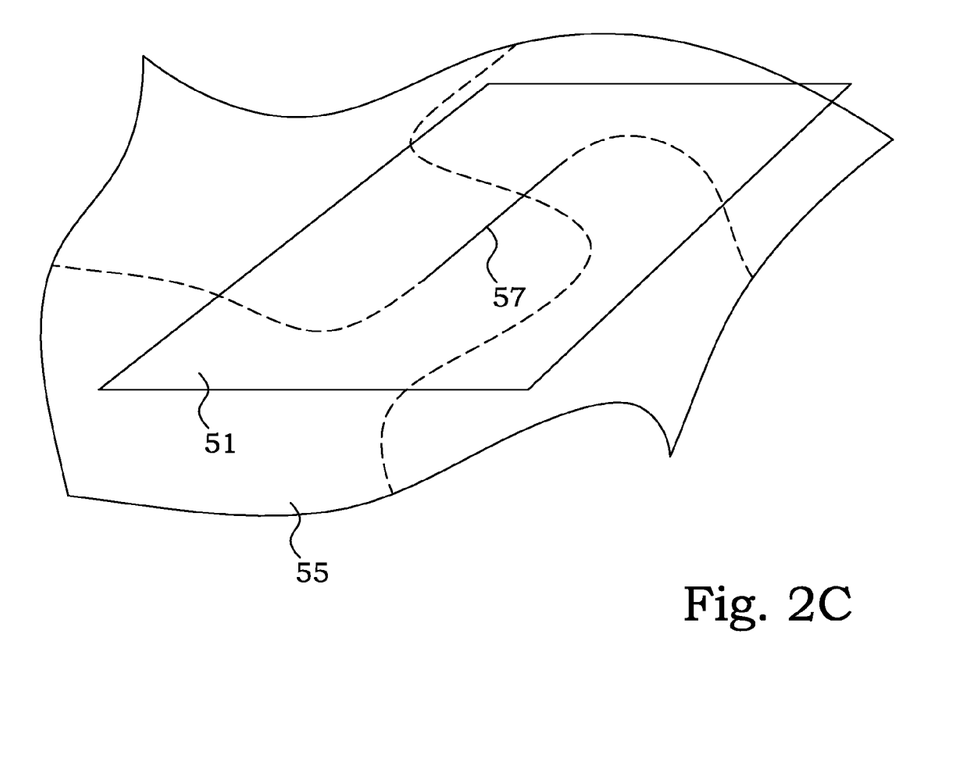

A doubly curved electrochromic device has permanently a non-flat shape with more than one principal curvature. A double curved surface 55, as shown in FIG. 2B, has a tangential plane 51 defined in at least one specific point 56 that is not in contact with the surface 55 along a straight line all the way to the edge of the surface. Examples of such surfaces are spherical, ellipsoidal or toroidal surfaces or more complex surfaces where the curvature may vary at different parts of the surface. One such example is shown in FIG. 2C, where the tangential plane 51 has a line contact 57 with the surface 55, but only over a certain limited distance.

Another way to look at the surface shapes is by defining curvatures. Optical devices with simple shapes, such as visors, mirrors and windows have typically two curvatures. A window with a flat surface has both radii of curvature equal to infinity. A visor with a cylindrical surface has one radius of curvature equal to infinity while the other curvature is finite. A fighter pilot visor with a spherical surface has both radii of curvatures equal to one another and finite. Many optical devices, such as goggles and helmet visors have toroidal surfaces with both radii of curvatures finite but non-equal. If the curvatures also change, the surface may be referred to as complex.

Forming is the process of permanently transforming a thermoplastic substrate (in the present invention with coating) from a flat shape into a non-flat shape. Thermoforming is an example of such a forming method, heating the substrate before and/or during the forming process, and will be discussed somewhat more in detail further below.

Thermoforming of plastic substrates has been described in the published U.S. patent application No. 2003/0052838. In this case the substrates are parts of a liquid crystal device comprising layers of indium tin oxide. However, the properties and requirements of liquid crystal devices are not directly comparable to electrochromic devices. Further precautions have to be considered. For larger electrochromic devices, above a certain minimum size, the sheet resistance of the transparent conductor determines the switching speed. The uniformity of the transparent conductor layer is furthermore crucial to the color uniformity of the electrochromic device. A more conductive area will exhibit faster switching than a less conductive area, this will not only result in a non-uniform coloration time but also, due to continuous overcharging, decrease the lifetime of the high conductive area.

Thermoforming of electrochromic materials has never been reported in prior art. The reason could be that several tentative risks for damaging the electrochromic properties could be thought of, and it is not obvious for anyone skilled in the art that thermoforming is a possible approach. However, tests have shown that functioning electrochromic devices according to the principles of the present invention are realizable.

Some considerations have to be made. During the thermoforming process, one substrate is given a convex curvature and the other substrate is given a concave curvature. The electrochromic material on the convex substrate becomes more porous during the thermoforming and the electrochromic material on the concave substrate becomes denser and less porous during the thermoforming. The porosity of the electrochromic material is crucial for the insertion and extraction of ions and thus the optical performance. This means that the finally formed electrochromic device according to the present invention may have properties that are different from a corresponding flat electrochromic device. The properties of the different layers in the electrochromic stack as deposited may have to be adjusted in order to acquire requested electrochromic properties in the finally formed device.

Due to the bending of the porous microstructure a curved electrochromic device having changing curvatures over the surface may have different optical behavior for each curvature. In such cases, the properties of the different layers in the electrochromic stack as deposited may even have to be adjusted between different part surfaces. However, the changes in properties introduced by the thermoforming process are reproducible. This means that once an appropriate adjustment of the layers as deposited has been found, the thermoforming process will always produce the requested electrochromic properties of the curved device.

Figure 3A:
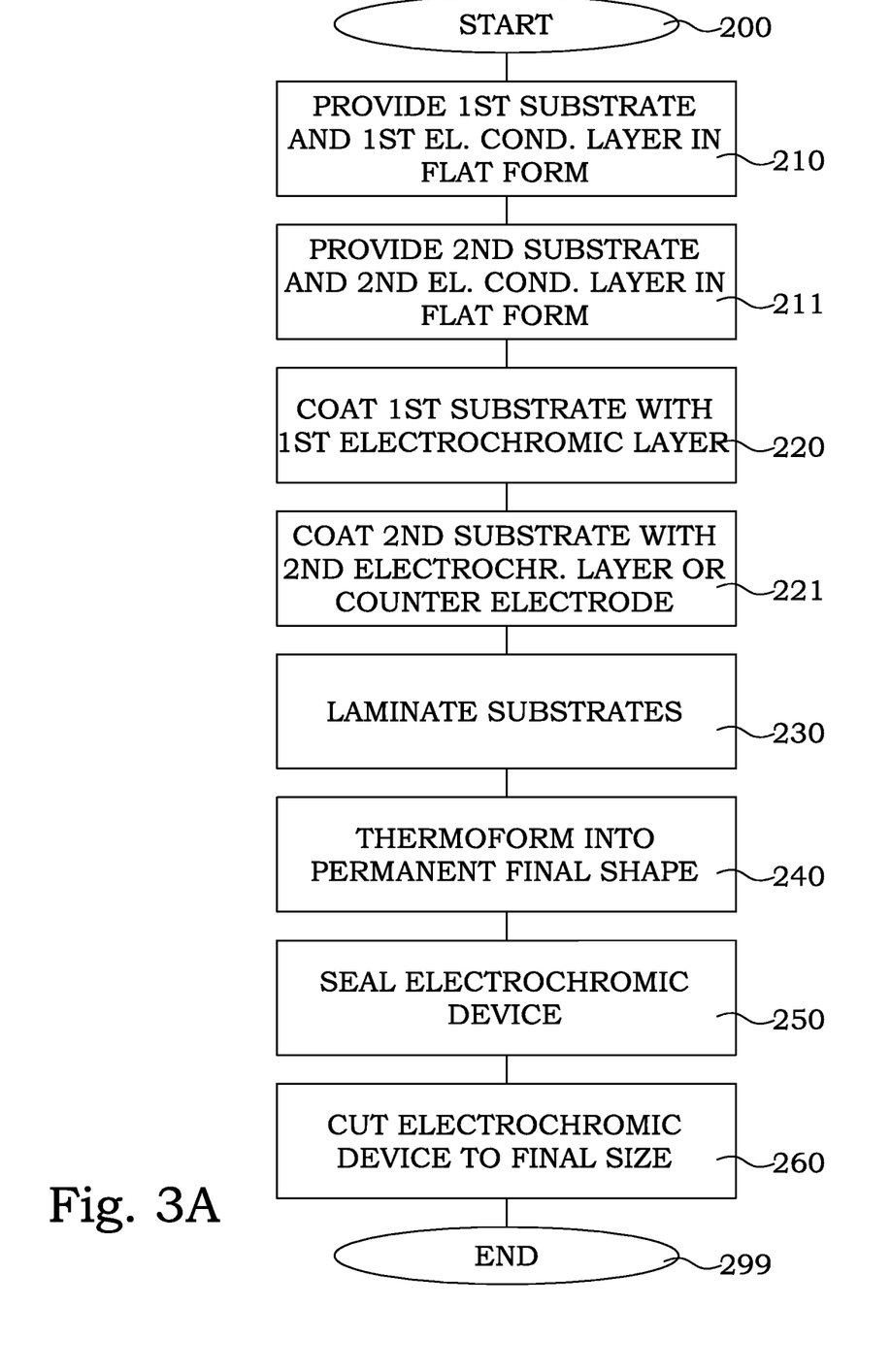
FIGS. 3A-C are flow diagrams of main steps of embodiments of methods according to the present invention.

FIG. 3A illustrates a flow diagram of main steps of an embodiment of a method according to the present invention. The procedure begins in step 200. In step 210 a first sheet comprising a first thermoplastic substrate at least partially coated with a first electron conducting layer is provided in a flat form. In step 211 a second sheet comprising a first thermoplastic substrate at least partially coated with a second electron conducting layer is provided in a flat form. The first sheet is at least partially coated by a first electrochromic layer in step 220 and said second sheet is at least partially coated by a counter electrode layer in step 221. In step 230 an electrolyte layer is interposed between the electrochromic half cells and the first sheet, the second sheet and the electrolyte layer are laminated into an electrochromic laminate sheet. The electrochromic laminate sheet is plastically formed into a permanent final curved shape in step 240, i.e. in the present embodiment after the lamination. The first sheet and the second sheet are therefore jointly formed. In step 250, the formed electrochromic laminate sheet is sealed and in step 260 cut into its final size. The procedure ends in step 299.

Figure 3B:
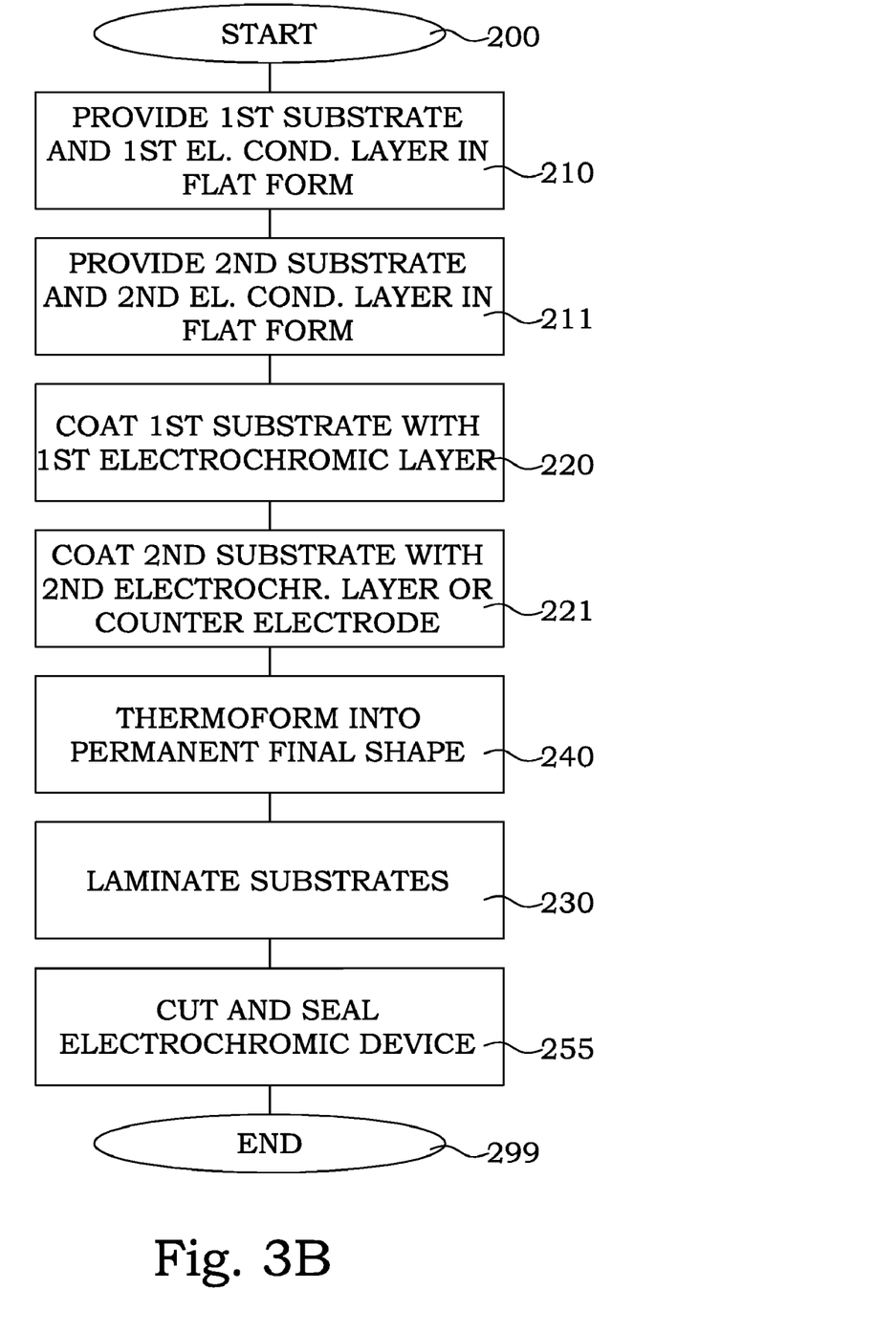

FIG. 3B illustrates a flow diagram of main steps of another embodiment of a method according to the present invention. Most steps are similar to those in FIG. 3A. However, in this embodiment, the thermoforming step occurs between the coating and laminating steps. Therefore, in the present embodiment, in step 240, the first sheet and the second sheet are separately plastically formed into respective permanent final curved shapes. The laminating step 230 in the present embodiment is therefore performed with curved electrochromic half cells. Moreover, in the present embodiment, the separate sealing and cutting steps are replaced by a step 255 simultaneously sealing and cutting the electrochromic device into its final size.

Figure 3C:
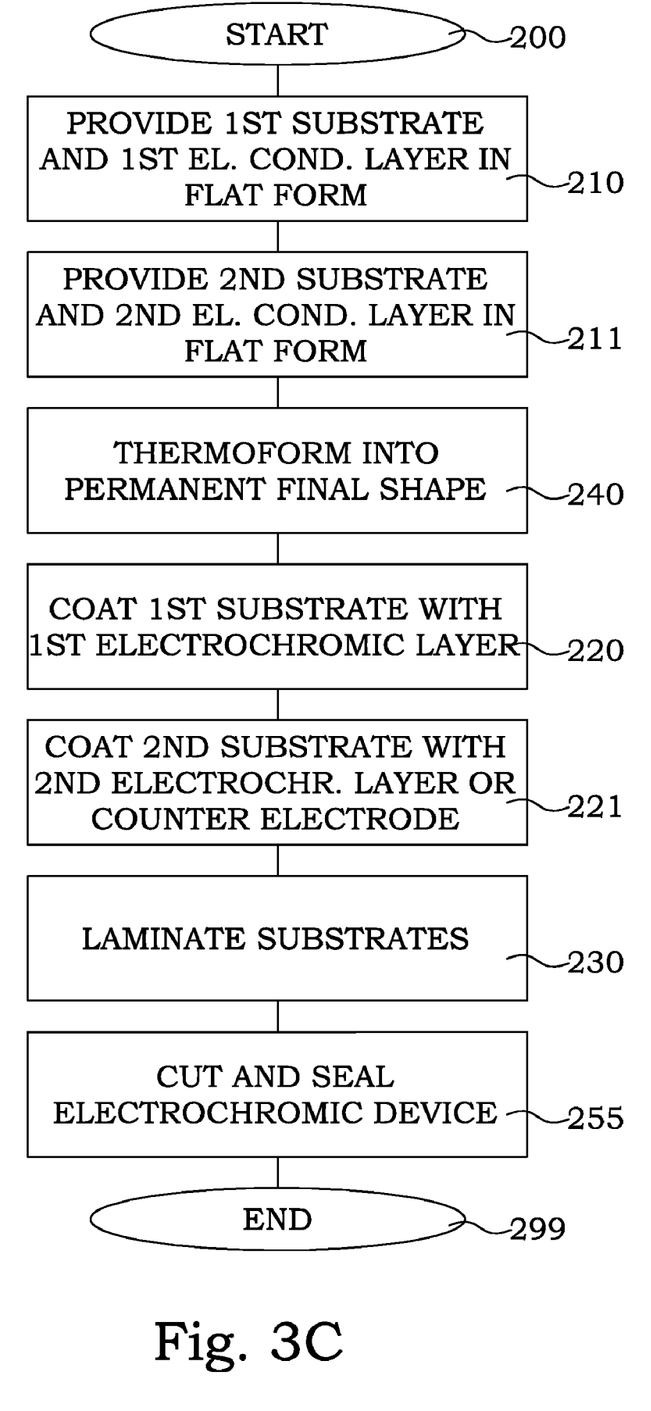

FIG. 3C illustrates a flow diagram of main steps of another embodiment of a method according to the present invention. Most steps are similar to those in FIGS. 3A and 3B. However, in this embodiment, the thermoforming step occurs between the providing steps and the coating steps. Therefore, in the present embodiment, in step 240, the first sheet and the second sheet are separately plastically formed into respective permanent final curved shapes. The coating steps 220 and 221 are therefore performed on curved substrates. The thermoforming step is, however, performed after the steps of providing the first sheet and the second sheet, which means that the provision of the electron conducting layers is performed on a flat surface.

Having the influences from the embodiments of FIGS. 3A-C, anyone skilled in the art realises that the thermoforming step according to the present invention can occur at any stage after at least the step of providing a first sheet and the step of providing a second sheet. For instance, the thermoforming could also occur after the sealing step.

In many cases, additional layers may be provided in the electrochromic half cells. Non-exclusive examples of such layers are bus bars or chemical compatibility layers. The thermoforming process can then be performed before or after such provision of additional layers.

Also outer layers, such as anti-scratch layers, anti-fog layers, anti-reflection layers, diffusion barriers, photocatalytic layers and specularly or diffusively reflecting layers, intended to cover the surface of an electrochromic device may be applied also with the present invention. The thermoforming process can then be performed before or after such provision of outer layers.

The preferred occasion for performing the thermoforming process depends e.g. on the actual application of the curved electrochromic device. If the deposition of different layers is difficult to provide on curved substrates, it is preferred to perform the thermoforming process after such depositions. On the other hand, if the thermoforming is believed to give rise to functional problems, e.g. cracking or flaking off of layers, it is preferable to perform the thermoforming process before deposition of such layers. Generally speaking, the thermoforming step should typically be performed as late as possible, without risking the performance quality of the electrochromic device.

As discussed in the summary section, the present invention is well adapted to mass production of electrochromic devices. Coating and lamination can be performed on flat thermoplastic substrates, which e.g. allows for roll to roll processing, e.g. in the procedures according to FIGS. 3A and 3B. Storage and transportation of semi-products can benefit from a flat or rolled structure of large pieces of material. A late thermoforming into curved shapes reduces required storage and transportation volumes and is thus well compatible with large production volumes Below, a number of examples will follow, illustrating some different variations in different parameters in some performed tests.

Figure 4A:
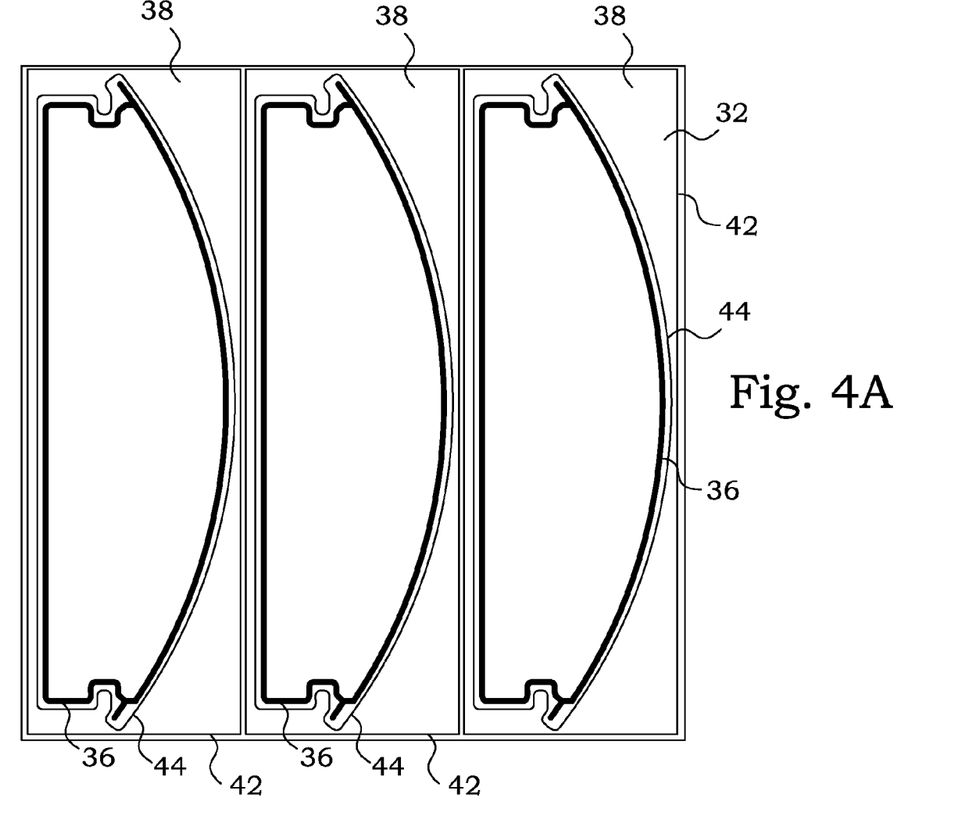
FIGS. 4A-E, 5A-E, 6 and 7A-B are schematic drawings of embodiments of electrochromic laminate sheets used in manufacturing according to the present invention.
Figure 4B:
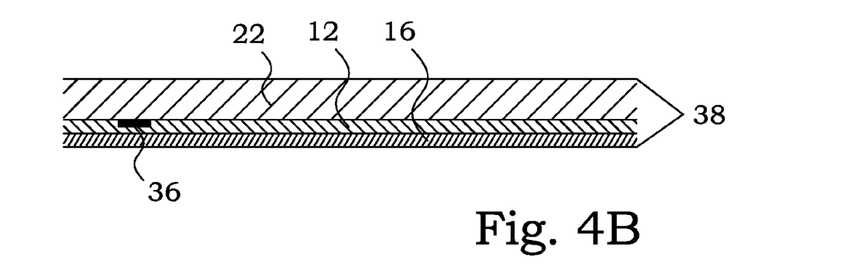

Example 1 concerns the manufacturing of a motorcycle helmet visor electrochromic device. In FIGS. 4A and 4B, a flat electrochromic half cell sheet 32 is illustrated in a top view and a cross-sectional view, respectively. A polyester substrate 22, 175 micrometer thick, is provided. The substrate 22 is coated by an electron conducting layer 12 of ITO, typically 50-400 nm thick, and an electrochromic layer 16 of hydrogen-containing Tungsten oxide, typically 50-1000 nm thick. Both layers 12 and 16 are deposited by magnetron sputtering. A bus bar 36 is included in the structure. The bus bar 36 is in the present example positioned between the layers 22 and 12, but may in another embodiment instead be placed between layers 12 and 16.

Figure 4C:
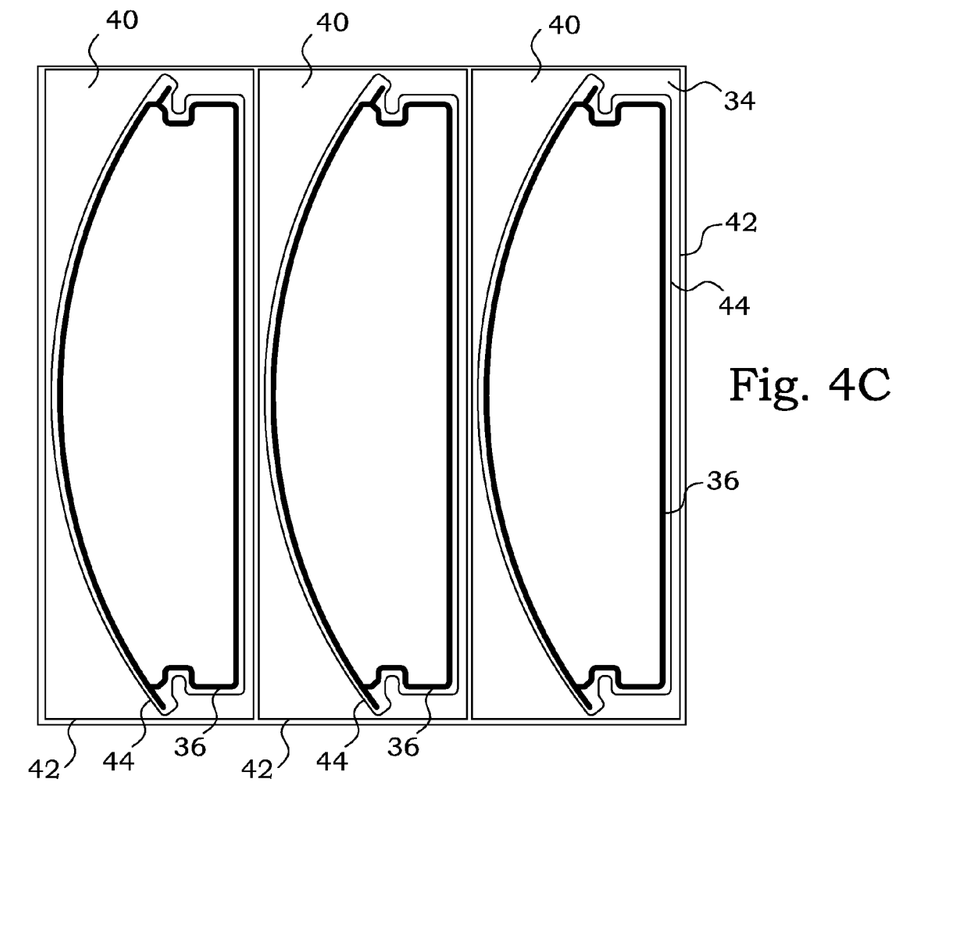
Figure 4D:
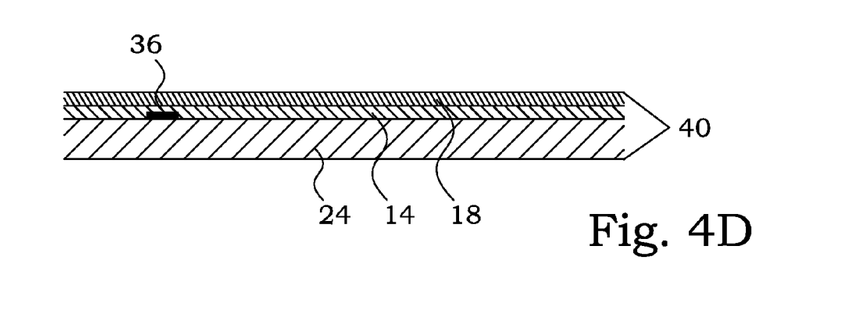

In FIGS. 4C and 4D, a corresponding flat opposite electrochromic half cell sheet 34 is illustrated in a top view and a cross-sectional view, respectively.

A polyester substrate 24, 175 micrometer thick, is provided. The substrate 24 is coated by an electron conducting layer 14 of ITO, typically 50-400 nm thick, and a counter electrode layer 18 of nickel-based oxide, typically 50-1000 nm thick. Both layers 14 and 18 are deposited by magnetron sputtering. A bus bar 36 is included in the structure. The bus bar 36 is in the present example positioned between the layers 24 and 14, but may in another embodiment instead be placed between layers 14 and 18.

The half cell sheet 34 with nickel-based oxide layer 18 is exposed to pretreatment as disclosed in the U.S. Pat. No. 6,500,287.

From each of the half cell sheet 32 and the half cell sheet 34, in total six electrochromic half cells 38, 40 are cut out along a line 42. The cutting may for instance be performed with ultrasonic cutting, laser cutting, die cutting or with a knife. The electrochromic half cells 38 based on the substrate 22 are heated to 149° C. and thermoformed into a convex doubly curved shape suitable for motorcycle helmet visor. Similarly, the electrochromic half cells 40 from the substrate 24 are heated to 149° C. and thermoformed into a concave doubly curved shape suitable for motorcycle helmet visor.

A line of a PMMA based electrolyte 20 is dispensed onto the convex 38 or onto the concave 40 electrochromic half cell. The convex and the concave electrochromic half cells 38, 40 are laminated together by roll-pressing so that a laminated electrochromic device 30 with a continuous layer 20 of electrolyte, typically 1-100 micrometer thick, in the middle is created, as illustrated in the cross-sectional view of FIG. 4E. Alternatively, the electrolyte 20 may be applied by spraying, screen printing or any similar techniques.

Figure 4E:
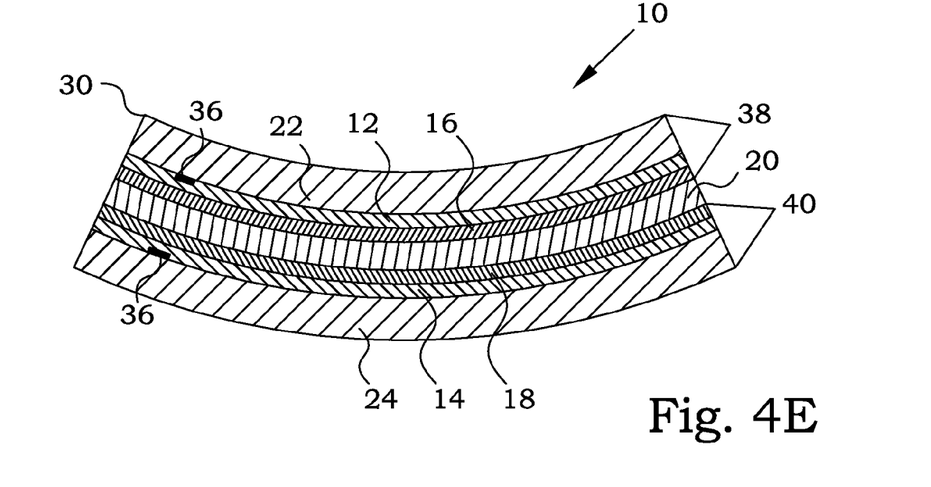

The electrochromic devices 30 are sealed along the lines 44 and electrically connected.

Figure 5A:
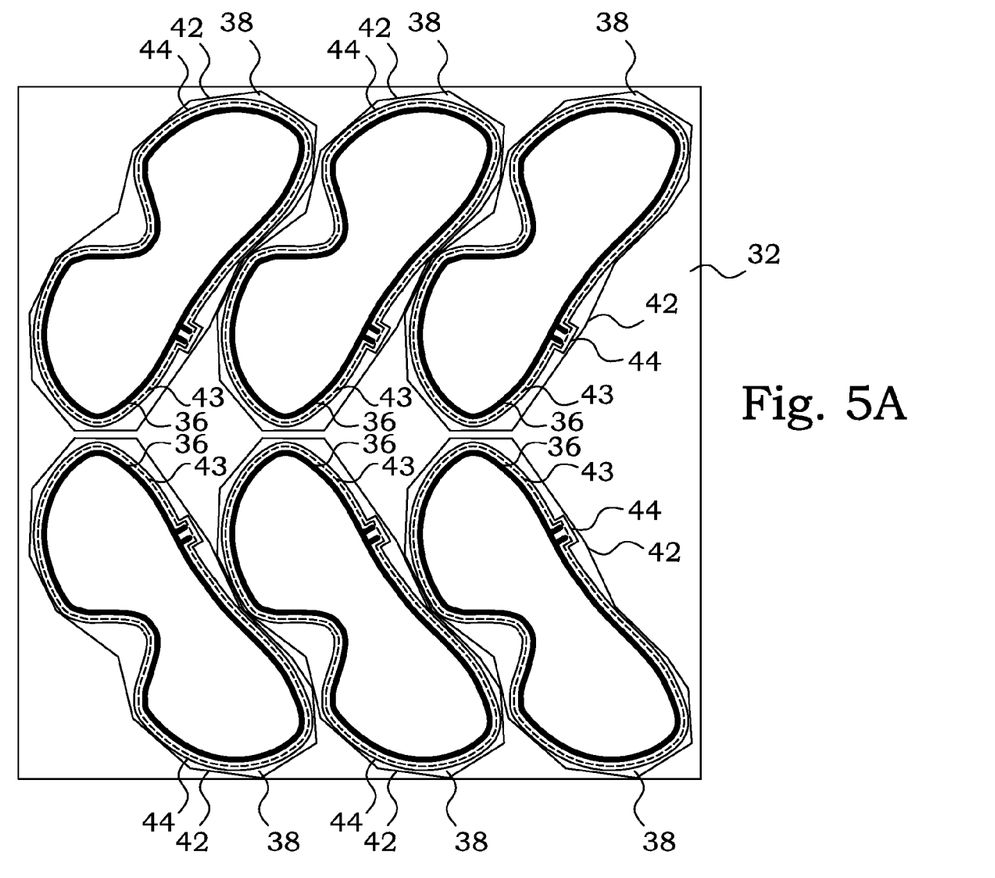
Figure 5B:
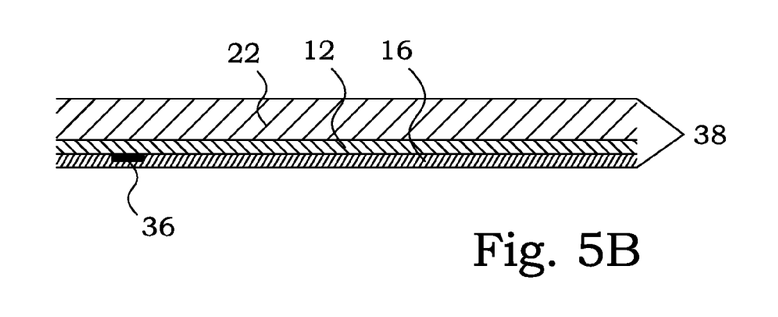

Example 2 concerns the manufacturing of a ski goggle electrochromic device. In FIGS. 5A and 5B, a flat electrochromic half cell sheet 32 for making six electrochromic devices is illustrated in a top view and a cross-sectional part view, respectively. A cellulose propionate substrate 22, 300 micrometer thick and 35 cm×35 cm large, is provided. In this example, the thickness of the cellulose propionate has been chosen to fit in a ski goggle frame. The substrate 22 is coated by an electron conducting layer 12 of ITO, typically 50-400 nm thick, and an electrochromic layer 16 of hydrogen-containing Tungsten oxide, typically 50-1000 nm thick. Both layers 12 and 16 are deposited by magnetron sputtering within areas encircled by the broken lines 43. A bus bar 36 is included in the structure. The bus bar 36 is in the present example positioned between the layers 16 and 12, but may in another embodiment instead be placed between layers 12 and 22.

Figure 5C:
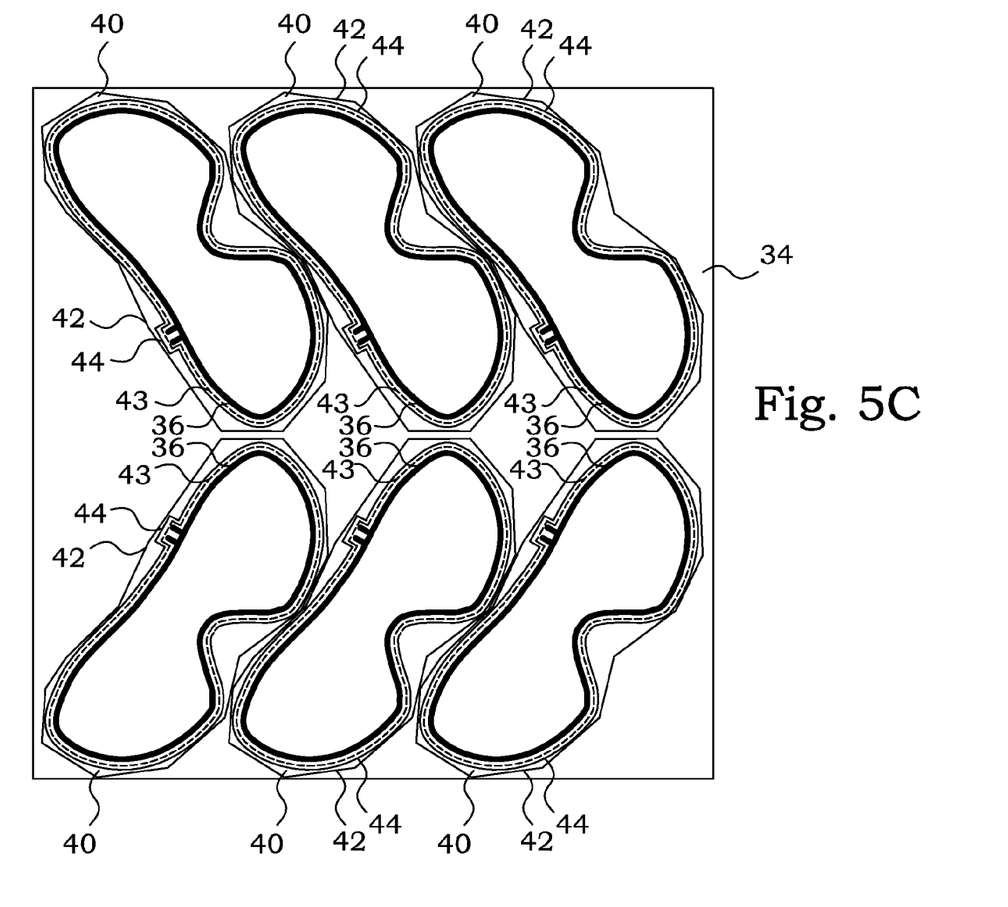
Figure 5D:
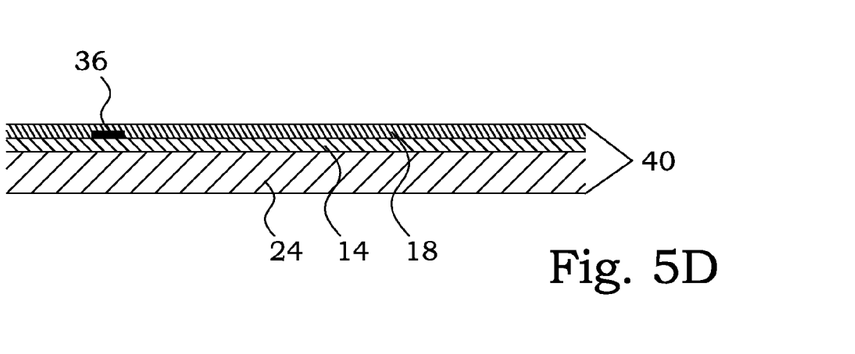

In FIGS. 5C and 5D, a corresponding flat opposite electrochromic half cell sheet 34 is illustrated in a top view and a cross-sectional part view, respectively. A cellulose propionate substrate 24, 300 micrometer thick and 35 cm×35 cm large, is provided. The substrate 24 is coated by an electron conducting layer 14 of ITO, typically 50-400 nm thick, and a counter electrode layer 18 of nickel-based oxide, typically 50-1000 nm thick. Both layers 14 and 18 are deposited by magnetron sputtering within areas encircled by the broken lines 43. A bus bar 36 is included in the structure. The bus bar 36 is in the present example positioned between the layers 18 and 14, but may in another embodiment instead be placed between layers 14 and 24.

The half cell sheet 34 with nickel-based oxide layer 18 is exposed to pretreatment as disclosed in the U.S. Pat. No. 6,500,287.

A line of a PMMA based electrolyte 20 is dispensed onto one of the electrochromic half cell sheets 32, 34. Both electrochromic half cell sheets 32, 34 are laminated together by roll-pressing so that an electrochromic laminated sheet with a continuous layer 20 of electrolyte, typically 1-100 micrometer thick, in the middle is created, as illustrated in the cross-sectional view of FIG. 5E. Alternatively, the electrolyte 20 may be applied by screen printing or spraying.

Figure 5E:
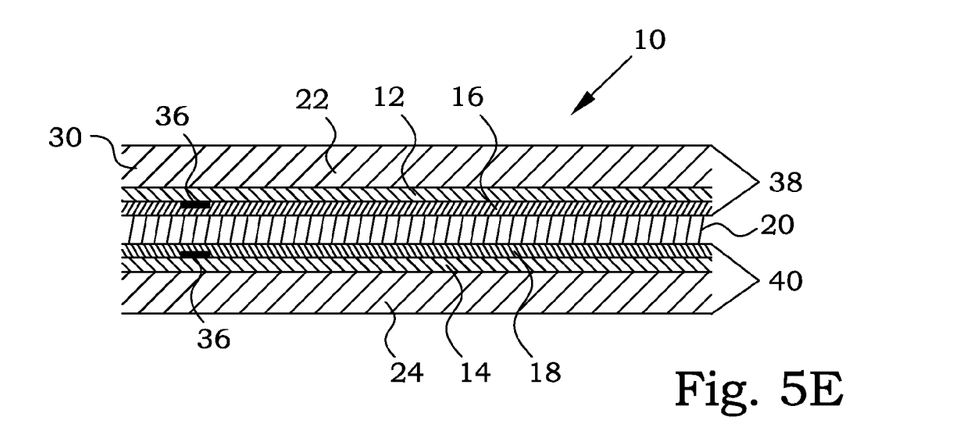

From the electrochromic laminated sheet six electrochromic devices 30 are cut out along the lines 42. The cutting may for instance be performed with ultrasonic cutting, laser cutting, die cutting or with a knife. The electrochromic devices 30 are heated to 56° C. and thermoformed into a doubly curved shape suitable for ski goggles The thermoforming can be performed in different ways. In the present example above, a commercial thermoforming apparatus (LEMA CPL 32) was utilised. The cut-out electrochromic devices are clamped against a clamp frame, thereby defining a volume between the electrochromic device and a female mould. The electrochromic device is gently heated to the required temperature in order to avoid overheating of the surface. A vacuum is applied to the volume between the electrochromic device and a female mould, whereby the heated electrochromic device forms against the female mould. The device is allowed to cool down and is removed from the mould.

Anyone skilled in the art realises that the details of the thermoforming can be performed in different manners, and that all types of thermoforming giving a plastic shape change into a permanent final curved shape can be utilised by the present invention. Non-exclusive examples could be thermoforming based on application of compressed air or mechanical pressing means.

The electrochromic devices 30 are sealed along the lines 44 and electrically connected.

Example 3 also concerns the manufacturing of a ski goggle electrochromic device. FIGS. 5A and 5B can be used as illustration also in this case. A polyester substrate 22, 175 micrometer thick and 35 cm×35 cm large, is provided. The substrate 22 is coated by an electron conducting layer 12 of ITO, typically 50-400 nm thick, and an electrochromic layer 16 of hydrogen-containing Tungsten oxide, typically 50-1000 nm thick. Both layers 12 and 16 are deposited by magnetron sputtering. A bus bar 36 is included in the structure. The bus bar 36 is in the present example positioned between the layers 22 and 12, but may in another embodiment instead be placed between layers 12 and 16.

FIGS. 5C and 5D can be used to illustrate also the second half cell of the present example. A polyester substrate 24, 175 micrometer thick and 35 cm×35 cm large, is provided. The substrate 24 is coated by an electron conducting layer 14 of ITO, typically 50-400 nm thick, and a counter electrode layer 18 of nickel-based oxide, typically 50-1000 nm thick. Both layers 14 and 18 are deposited by magnetron sputtering. A bus bar 36 is included in the structure. The bus bar 36 is in the present example positioned between the layers 24 and 14, but may in another embodiment instead be placed between layers 14 and 18.

Figure 6:
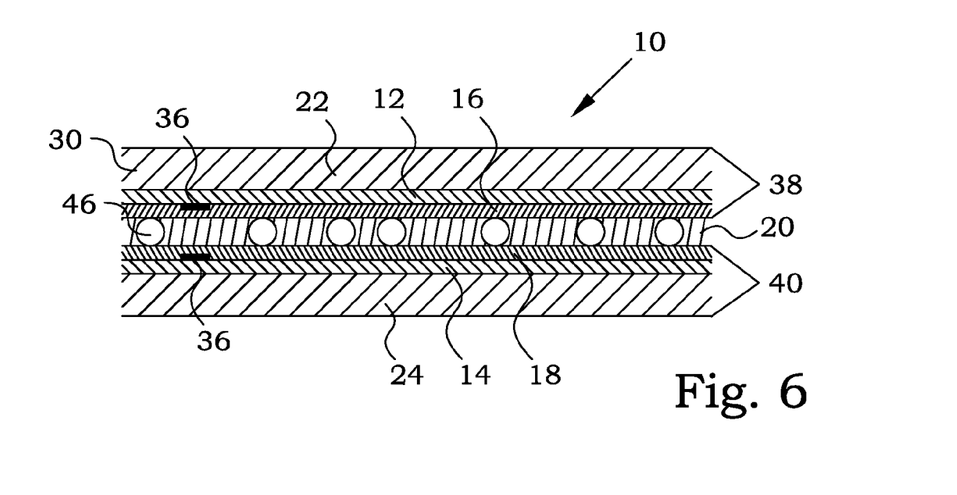

In the present example, illustrated by FIG. 6, spherical spacers 46 are used in the electrolyte layer 20. Before lamination, spherical spacers 46 are dispensed onto the electrochromic layer 16 with a spray nozzle. The spacers 46 are mixed in a liquid and transported to the spray nozzle through a pump, and subsequently sprayed on the substrate from the nozzle with high pressure. The liquid is evaporated and the spacer 46 population is monitored after spraying. The spacers 46 are dispensed evenly in order to secure a fixed gap when laminating the electrochromic half cell sheets 32, 34. The diameter of the spherical spacers 46 is in this embodiment 10 microns, available e.g. by Merck.

A line of a PMMA-based electrolyte 20 is dispensed onto one of the electrochromic half cell sheets 32, 34. Both electrochromic half cell sheets 32, 34 are laminated together by roll-pressing so that an electrochromic laminated sheet with a continuous layer 20 of electrolyte, 10 micrometer thick, in the middle of the laminate is created, as illustrated in the cross-sectional view of FIG. 6. Alternatively, the electrolyte 20 may be applied by screen printing or spraying.

From the electrochromic laminated sheet six electrochromic devices 30 are cut out and simultaneously sealed along the lines 44.

The electrochromic devices 30 are heated to 149° C. and thermoformed into a double curvature suitable for goggles for motor sports. The electrochromic devices are finally electrically connected.

Example 4 also concerns the manufacturing of helmet visor electrochromic devices. FIG. 4A can be used as illustration also in this case. A cellulose acetate substrate 22, 500 micrometer thick and 35 cm×35 cm large, is provided. A bus bar 36 is included in the structure on top of the substrate 22. The substrate 22 and the bus bar 36 are coated by an electron conducting layer 12 of ITO, typically 50-400 nm thick. The conducting layer 12 is deposited by magnetron sputtering.

FIG. 4C can be used to illustrate also the second half cell of the present example. The substrate 24 consists of polycarbonate, 1000 micrometer thick and 35 cm×35 cm large. A bus bar 36 is included in the structure on top of the substrate 24. The bus bar and the substrate 24 are coated by an electron conducting layer 14 of ITO, typically 50-400 nm thick. The conducting layer 12 is deposited by magnetron sputtering.

Figure 7A:
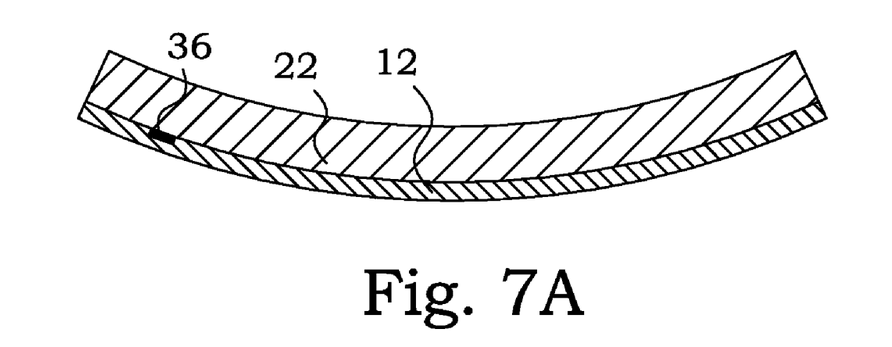
Figure 7B:
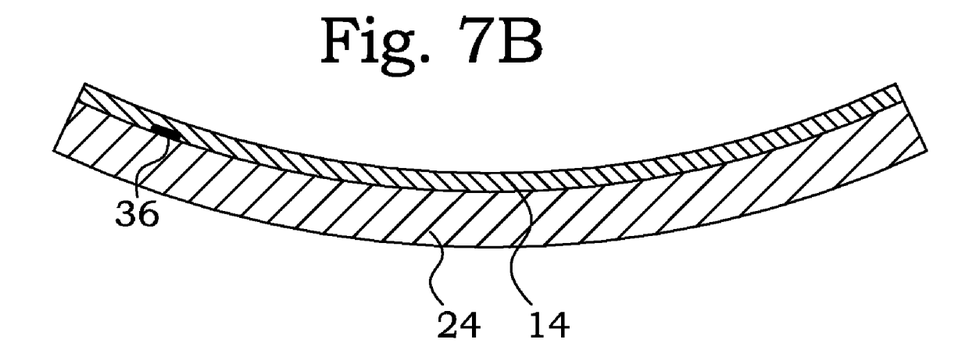

In total six pieces are cut out from the first substrate 22 and the second substrate 24 along a line 42. The pieces from substrate 22 are heated to 60° C. and thermoformed into a convex doubly curved shape suitable for helmet visors. The pieces from substrate 24 are heated to 199° C. and thermoformed into a concave doubly curved shape suitable for helmet visors. The formed pieces are schematically illustrated in FIGS. 7A and 7B.

The ITO coated and curved first substrate 22 is coated, at least partially, by an electrochromic layer 16 of hydrogen-containing Tungsten oxide, typically 50-1000 nm thick. The ITO coated and curved second substrate 24 is coated, at least partially, by a counter electrode layer 18 of nickel-based oxide, typically 50-1000 nm thick. Both layers 16 and 18 are deposited by magnetron sputtering. The substrate 24 with nickel-based oxide layer 18 is exposed to pretreatment as disclosed in the U.S. Pat. No. 6,500,287.

A line of a PMMA based electrolyte 20 is dispensed onto the convex 38 or onto the concave 40 electrochromic half cell. The convex and the concave electrochromic half cells 38, 40 are laminated together by roll-pressing so that a laminated electrochromic device 30 with a continuous layer 20 of electrolyte, typically 1-100 micrometer thick, in the middle is created, as illustrated in the cross-sectional view of FIG. 4E. Alternatively, the electrolyte 20 may be applied by spraying.

The electrochromic devices 30 are sealed along the lines 44 and electrically connected.

The area coated by ITO, tungsten oxide and nickel oxide in examples 1-4 above may extend fully or partly over the plastic substrates. Spacers may also be added to the electrolyte to ensure that the distance between the laminated electrochromic half cells are kept constant during the thermoforming and laminating process.

In the above examples, the plastic substrates 22, 24 have been specified by composition and thickness. However, the present invention is not restricted to such situations. According to the present invention it is also possible to use other plastic substrates 22, 24 of differing materials and thickness.

The specific shape, dimensions and number of electrochromic devices made from one laminated sheet in the above examples are only presented for illustration purposes. None of the dimensions is critical to or limiting the use of the present method of production of electrochromic devices. Therefore, electrochromic devices of other sizes and shapes can easily be made.

Other electrochromic layers than tungsten-based oxide, other counter electrode layers than nickel-based oxide, other electron conductors than ITO, and other ion conductors than PMMA-based polymers may be used, e.g. the examples mentioned in the beginning of the detailed description. Furthermore, other plastics may be used for substrates. Also, additional layers, such as disclosed in U.S. Pat. No. 6,211,995, may be included in the electrochromic stack. Additional coatings, such as anti-scratch, anti-fog, anti-reflection, diffusion barrier, photocathalytic, reflecting layers, may be applied on the outside of the plastic substrates. The thermoforming can be performed before or after such additional coatings.

The embodiments and examples described above are thus to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

WO 9923528 (U.S. Pat. No. 6,404,532)
U.S. Pat. No. 5,953,150
US 2004/0253401
U.S. Pat. No. 5,805,367
US 2003/0052838
U.S. Pat. No. 6,500,287
U.S. Pat. No. 6,211,995
"Handbook of inorganic electrochromic materials", pp. 19-63 (chapter 2-4), by C. G. Granqvist, Elsevier 2002

The invention claimed is:

1. Method for manufacturing of curved electrochromic devices, comprising the steps of:
   providing a first sheet comprising a first thermoplastic substrate at least partially coated with a first electron conducting layer in a flat form;
   providing a second sheet comprising a second thermoplastic substrate at least partially coated with a second electron conducting layer in a flat form;
   coating said first sheet at least partially by a first electrochromic layer;
   coating said second sheet at least partially by a counter electrode layer;
   laminating an electrolyte layer interposed between said first sheet and said second sheet into an electrochromic laminate sheet;
   thermoforming said first sheet and said second sheet into a permanent final curved shape after at least said step of providing a first sheet and said step of providing a second sheet; and
   sealing said electrochromic laminate sheet;
   wherein said step of thermoforming is performed jointly on said first sheet and said second sheet before said step of sealing.

2. Method according to claim 1, comprising the further step of:
   providing said first electrochromic layer at least partially with an additional layer, providing said counter electrode layer with an additional layer, providing said first electron conducting layer at least partially with an additional layer and/or providing said second electron conducting layer at least partially with an additional layer.

3. Method according to claim 2, wherein said additional layer is selected from the list of:
   bus bar; and
   chemical compatibility layer.

4. Method according to claim 1, comprising the further step of providing an outer surface of said electrochromic device with at least one outer layer.

5. Method according to claim 4, wherein said outer layer is selected from the list of:
   anti-scratch layer;
   anti-fog layer;
   anti-reflection layer;
   diffusion barrier;
   photocatalytic layer; and
   specularly or diffusively reflecting layer.

6. Method according to claim 1, wherein said step of thermoforming is performed jointly on said first sheet and said second sheet after said step of laminating.

7. Method according to claim 4, wherein said step of thermoforming is performed jointly on said first sheet and said second sheet after said step of providing an outer surface of said electrochromic device with at least one outer layer.

8. Method according to claim 6, comprising the further step of providing spacer particles onto said first electrochromic layer and/or said counter electrode layer before said step of laminating.

9. Method according to claim 6, wherein said step of laminating is performed in the absence of spacer particles between said first electrochromic layer and said counter electrode layer.

10. Method according to claim 1, wherein said curved electrochromic devices are doubly curved electrochromic devices.

11. Electrochromic device, manufactured by a method according to the steps:
   providing a first sheet comprising a first thermoplastic substrate at least partially coated with a first electron conducting layer in a flat form;
   providing a second sheet comprising a second thermoplastic substrate at least partially coated with a second electron conducting layer in a flat form;
   coating said first sheet at least partially by a first electrochromic layer;
   coating said second sheet at least partially by a counter electrode layer;
   laminating an electrolyte layer interposed between said first sheet and said second sheet into an electrochromic laminate sheet;

thermoforming said first sheet and said second sheet into a permanent final curved shape after at least said step of providing a first sheet and said step of providing a second sheet; and sealing said electrochromic laminate sheet;

wherein said step of thermoforming is performed jointly on said first sheet and said second sheet before said step of sealing.

* * * * *